(12) United States Patent
Seavey et al.

(10) Patent No.: US 9,907,551 B2
(45) Date of Patent: Mar. 6, 2018

(54) SURGICAL INSTRUMENT FOR IMPLANTING FIXATION DEVICE

(71) Applicant: Howmedica Osteonics Corp., Mahwah, NJ (US)

(72) Inventors: Jeffrey F. Seavey, Houston, TX (US); Lance N. Terrill, League City, TX (US); Andrew Palmer, Orlando, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 147 days.

(21) Appl. No.: 14/817,333

(22) Filed: Aug. 4, 2015

(65) Prior Publication Data

US 2016/0030039 A1    Feb. 4, 2016

Related U.S. Application Data

(60) Provisional application No. 62/032,905, filed on Aug. 4, 2014.

(51) Int. Cl.
*A61B 17/068* (2006.01)
*A61B 17/064* (2006.01)
(Continued)

(52) U.S. Cl.
CPC ...... *A61B 17/0642* (2013.01); *A61B 17/0682* (2013.01); *A61B 17/16* (2013.01); *A61B 50/30* (2016.02); *A61B 17/2833* (2013.01); *A61B 50/3001* (2016.02); *A61B 2017/0645* (2013.01); *A61B 2017/0688* (2013.01); *A61B 2017/2845* (2013.01)

(58) Field of Classification Search
CPC . A61B 17/0682; A61B 17/0642; A61B 17/16; A61B 17/2833; A61B 17/2812; A61B 50/30; A61B 50/3001; A61B 2017/0688; A61B 2017/2845; A61B 2017/0645
See application file for complete search history.

(56) References Cited

U.S. PATENT DOCUMENTS 1,427,668 A * 8/1922 Williams ............... B25B 7/16
                                                        81/320
1,534,066 A * 4/1925 Larkey ............... B25B 27/062
                                                        29/261
(Continued)

FOREIGN PATENT DOCUMENTS

DE    3337447 A1    5/1985
DE    4110123 A1    10/1992
(Continued)

OTHER PUBLICATIONS

International Search Report and Written Opinion for Application PCT/IB2013/05200 dated Dec. 16, 2013.
(Continued)

*Primary Examiner* — Andrew M Tecco
(74) *Attorney, Agent, or Firm* — Lerner, David, Littenberg, Krumholz & Mentlik, LLP

(57) ABSTRACT

A surgical spreader assembly for use in implanting staples and other implants in a patient is disclosed. The spreader assembly may be included a kit with a number of other surgical instruments and the staples for implantation in the patient.

20 Claims, 14 Drawing Sheets

(51) Int. Cl.
    *A61B 17/16*     (2006.01)
    *A61B 50/30*     (2016.01)
    *A61B 17/28*     (2006.01)

(56) References Cited

U.S. PATENT DOCUMENTS

| | | | |
|---|---|---|---|
| 2,222,744 A | 11/1940 | Gallien, Jr. | |
| 3,041,712 A * | 7/1962 | Wurzel | B25B 27/205 |
| | | | 29/229 |
| 3,926,195 A | 12/1975 | Bleier et al. | |
| 3,960,147 A | 6/1976 | Murray | |
| 4,280,265 A * | 7/1981 | Murphy | B25B 27/205 |
| | | | 29/229 |
| 4,438,769 A | 3/1984 | Pratt et al. | |
| 4,462,395 A | 7/1984 | Johnson | |
| 4,462,404 A | 7/1984 | Schwarz et al. | |
| 4,511,035 A | 4/1985 | Alpern | |
| 4,538,485 A * | 9/1985 | Saila | B25B 7/16 |
| | | | 81/320 |
| 4,554,848 A * | 11/1985 | Galletto | B25B 7/02 |
| | | | 81/318 |
| 4,625,379 A * | 12/1986 | Anderson | B25B 27/205 |
| | | | 29/229 |
| 4,723,540 A | 2/1988 | Gilmer, Jr. | |
| 4,841,960 A | 6/1989 | Garner | |
| 4,852,558 A | 8/1989 | Outerbridge | |
| 4,889,110 A | 12/1989 | Galline et al. | |
| 4,938,408 A | 7/1990 | Bedi et al. | |
| 4,951,861 A | 8/1990 | Schulze et al. | |
| 4,994,063 A | 2/1991 | Garner | |
| 5,089,009 A | 2/1992 | Green | |
| 5,141,514 A | 8/1992 | van Amelsfort | |
| 5,205,459 A | 4/1993 | Brinkerhoff et al. | |
| 5,222,975 A | 6/1993 | Crainich | |
| 5,242,457 A | 9/1993 | Akopov et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,340,360 A | 8/1994 | Stefanchik | |
| 5,342,373 A | 8/1994 | Stefanchik et al. | |
| 5,425,489 A | 6/1995 | Shichman et al. | |
| 5,439,479 A | 8/1995 | Shichman et al. | |
| 5,449,359 A | 9/1995 | Groiso | |
| 5,484,451 A | 1/1996 | Akopov et al. | |
| 5,660,188 A | 8/1997 | Groiso | |
| 5,662,655 A | 9/1997 | Laboureau et al. | |
| 5,697,933 A * | 12/1997 | Gundlapalli | A61B 17/1714 |
| | | | 606/206 |
| 5,788,698 A | 8/1998 | Savornin | |
| 5,833,697 A | 11/1998 | Ludwick | |
| 5,853,414 A | 12/1998 | Groiso | |
| 5,941,890 A | 8/1999 | Voegele et al. | |
| 5,947,999 A | 9/1999 | Groiso | |
| 5,993,476 A | 11/1999 | Groiso | |
| 6,145,417 A * | 11/2000 | Bates | B25B 27/205 |
| | | | 81/177.4 |
| 6,261,296 B1 | 7/2001 | Aebi et al. | |
| 6,287,310 B1 | 9/2001 | Fox | |
| 6,425,903 B1 | 7/2002 | Voegele | |
| 6,446,854 B1 | 9/2002 | Remiszewski et al. | |
| 6,635,072 B1 | 10/2003 | Ramamurti et al. | |
| 6,685,708 B2 | 2/2004 | Monassevitch et al. | |
| 6,716,226 B2 | 4/2004 | Sixto, Jr. et al. | |
| 6,726,705 B2 | 4/2004 | Peterson et al. | |
| 6,767,356 B2 | 7/2004 | Kanner et al. | |
| 6,907,992 B2 * | 6/2005 | McMichael | A61B 50/30 |
| | | | 206/370 |
| 6,969,391 B1 | 11/2005 | Gazzani | |
| 7,052,504 B2 | 5/2006 | Hughett | |
| 7,108,709 B2 | 9/2006 | Cummins | |
| 7,112,214 B2 | 9/2006 | Peterson et al. | |
| 7,189,234 B2 | 3/2007 | Zucherman et al. | |
| 7,211,092 B2 | 5/2007 | Hughett | |
| 7,240,677 B2 | 7/2007 | Fox | |
| D574,498 S | 8/2008 | Fox et al. | |
| 7,506,791 B2 | 3/2009 | Omaits et al. | |
| 7,533,790 B1 | 5/2009 | Knodel et al. | |
| 7,547,315 B2 | 6/2009 | Peterson et al. | |
| 7,552,853 B2 | 6/2009 | Mas et al. | |
| 7,611,038 B2 | 11/2009 | Racenet et al. | |
| 7,628,306 B2 | 12/2009 | Spurchise et al. | |
| 7,635,367 B2 * | 12/2009 | Groiso | A61B 17/0642 |
| | | | 606/75 |
| 7,651,498 B2 | 1/2010 | Shifrin et al. | |
| 7,669,747 B2 | 3/2010 | Weisenburgh, II et al. | |
| 7,727,245 B2 | 6/2010 | Bender et al. | |
| 7,735,703 B2 | 6/2010 | Morgan et al. | |
| 7,753,250 B2 | 7/2010 | Clauson et al. | |
| 7,766,208 B2 | 8/2010 | Epperly et al. | |
| 7,794,475 B2 | 9/2010 | Hess et al. | |
| D625,417 S | 10/2010 | Fox et al. | |
| 7,811,286 B2 | 10/2010 | Medoff | |
| 7,824,426 B2 | 11/2010 | Racenet et al. | |
| 7,934,630 B2 | 5/2011 | Shelton, IV et al. | |
| 7,942,877 B2 | 5/2011 | Medoff | |
| 8,006,839 B2 * | 8/2011 | Hafner | A61F 2/0095 |
| | | | 206/363 |
| 8,066,720 B2 | 11/2011 | Knodel et al. | |
| 8,074,860 B2 | 12/2011 | Yasuda | |
| 8,096,420 B2 * | 1/2012 | Marhsall | B65D 81/075 |
| | | | 206/363 |
| 8,123,101 B2 | 2/2012 | Racenet et al. | |
| 8,137,351 B2 * | 3/2012 | Prandi | A61B 17/0682 |
| | | | 606/75 |
| 8,186,560 B2 | 5/2012 | Hess et al. | |
| 8,211,109 B2 | 7/2012 | Groiso | |
| 8,211,126 B2 | 7/2012 | Yeh et al. | |
| 8,220,690 B2 | 7/2012 | Hess et al. | |
| D669,984 S | 10/2012 | Cheney et al. | |
| D669,985 S | 10/2012 | Cheney et al. | |
| 8,328,065 B2 | 12/2012 | Shah | |
| D675,734 S | 2/2013 | Cheney et al. | |
| D676,962 S | 2/2013 | Cheney et al. | |
| 8,365,976 B2 | 2/2013 | Hess et al. | |
| 8,372,075 B2 | 2/2013 | Groiso | |
| 8,393,254 B2 * | 3/2013 | Gao | A61B 17/2804 |
| | | | 294/2 |
| D691,720 S | 10/2013 | Cheney et al. | |
| D691,722 S | 10/2013 | Cheney | |
| 8,584,853 B2 | 11/2013 | Knight et al. | |
| D701,307 S | 3/2014 | Protopsaltis et al. | |
| 8,685,068 B2 | 4/2014 | Sixto et al. | |
| 8,701,890 B2 | 4/2014 | Bertazzoni et al. | |
| D705,930 S | 5/2014 | Cheney | |
| 8,721,646 B2 | 5/2014 | Fox | |
| D706,927 S | 6/2014 | Cheney et al. | |
| D707,357 S | 6/2014 | Cheney et al. | |
| 8,808,294 B2 | 8/2014 | Fox et al. | |
| 8,808,380 B2 | 8/2014 | Fox et al. | |
| 8,834,483 B2 | 9/2014 | Cheney et al. | |
| 8,881,900 B2 | 11/2014 | Witt et al. | |
| D723,688 S | 3/2015 | Knight | |
| 9,017,331 B2 | 4/2015 | Fox | |
| 9,034,037 B2 | 5/2015 | Fiere et al. | |
| 9,095,338 B2 * | 8/2015 | Taylor | A61B 17/0642 |
| 9,101,349 B2 | 8/2015 | Knight et al. | |
| 9,144,464 B2 * | 9/2015 | Knowlton | A61B 19/026 |
| 9,156,150 B2 * | 10/2015 | Wang | B25B 7/08 |
| 9,204,932 B2 | 12/2015 | Knight et al. | |
| 9,346,178 B2 * | 5/2016 | Tsai | B26B 13/26 |
| 2002/0029044 A1 | 3/2002 | Monassevitch et al. | |
| 2002/0072752 A1 | 6/2002 | Zucherman et al. | |
| 2005/0049600 A1 | 3/2005 | Groiso | |
| 2005/0082730 A1 * | 4/2005 | Murray | B25B 5/067 |
| | | | 269/166 |
| 2005/0273108 A1 | 12/2005 | Groiso | |
| 2006/0111721 A1 | 5/2006 | Puricelli et al. | |
| 2008/0082124 A1 | 4/2008 | Hess et al. | |
| 2008/0082125 A1 | 4/2008 | Murray et al. | |
| 2008/0161808 A1 | 7/2008 | Fox | |
| 2008/0173691 A1 | 7/2008 | Mas et al. | |
| 2008/0173692 A1 | 7/2008 | Spurchise et al. | |
| 2008/0177300 A1 | 7/2008 | Mas et al. | |

(56) References Cited

U.S. PATENT DOCUMENTS

| | | |
|---|---|---|
| 2009/0001125 A1 | 1/2009 | Hess et al. |
| 2009/0005807 A1 | 1/2009 | Hess et al. |
| 2009/0134198 A1 | 5/2009 | Knodel et al. |
| 2009/0242609 A1 | 10/2009 | Kanner |
| 2009/0259249 A1 | 10/2009 | Lobello |
| 2010/0063506 A1 | 3/2010 | Fox et al. |
| 2010/0082030 A1* | 4/2010 | Groiso ............... A61B 17/0642 606/75 |
| 2010/0087822 A1 | 4/2010 | Groiso |
| 2010/0133316 A1 | 6/2010 | Lizee et al. |
| 2010/0187283 A1 | 7/2010 | Crainich et al. |
| 2010/0191255 A1 | 7/2010 | Crainich et al. |
| 2010/0237128 A1 | 9/2010 | Miller et al. |
| 2010/0241142 A1* | 9/2010 | Akyuz ............... A61B 17/0469 606/144 |
| 2010/0318103 A1 | 12/2010 | Cheng et al. |
| 2011/0036736 A1* | 2/2011 | Knowlton ............ A61B 19/026 206/438 |
| 2011/0087276 A1 | 4/2011 | Bedi et al. |
| 2012/0080336 A1 | 4/2012 | Shelton, IV et al. |
| 2012/0080340 A1 | 4/2012 | Shelton, IV et al. |
| 2012/0080477 A1* | 4/2012 | Leimbach ........ A61B 17/07207 227/175.2 |
| 2012/0145765 A1 | 6/2012 | Peterson et al. |
| 2012/0228355 A1 | 9/2012 | Combrowski et al. |
| 2013/0026206 A1 | 1/2013 | Fox |
| 2013/0026207 A1 | 1/2013 | Fox |
| 2013/0030437 A1 | 1/2013 | Fox |
| 2013/0030438 A1 | 1/2013 | Fox |
| 2013/0065740 A1* | 3/2013 | Francis .............. A63B 21/0004 482/122 |
| 2013/0153627 A1 | 6/2013 | Euteneuer et al. |
| 2013/0153628 A1 | 6/2013 | Euteneuer |
| 2013/0206815 A1 | 8/2013 | Fox |
| 2013/0213843 A1 | 8/2013 | Knight et al. |
| 2013/0231667 A1 | 9/2013 | Taylor et al. |
| 2013/0256167 A1 | 10/2013 | Scott et al. |
| 2013/0319888 A1 | 12/2013 | Birkbeck et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0024002 A1 | 1/2014 | Knight et al. |
| 2014/0034702 A1 | 2/2014 | Miller et al. |
| 2014/0097228 A1 | 4/2014 | Taylor et al. |
| 2015/0321364 A1* | 11/2015 | Tsai ....................... B26B 13/26 30/262 |
| 2016/0000434 A1* | 1/2016 | Cocaign ............ A61B 17/0642 606/75 |

FOREIGN PATENT DOCUMENTS

| | | | |
|---|---|---|---|
| DE | 19725597 A1 | 10/1998 | |
| DE | 212008000029 U1 | 12/2009 | |
| EP | 0826340 A2 | 3/1998 | |
| EP | 1504723 A2 | 2/2005 | |
| FR | 1080876 A | 12/1954 | |
| WO | WO 2014140692 A1 * | 9/2014 | ......... A61B 17/0642 |

OTHER PUBLICATIONS

International Search Report and Written Opinion, PCT/FR2005/050245, dated Sep. 29, 2005.

* cited by examiner

SURGICAL INSTRUMENT FOR IMPLANTING FIXATION DEVICE

This application claims priority to U.S. Patent App. No. 62/032,905, which was filed on Aug. 4, 2014 and is expressly incorporated herein by reference.

TECHNICAL FIELD

The present disclosure relates generally to instruments for use in a surgical procedure, and, more specifically, to surgical instruments for use in implanting fixation devices into a patient.

BACKGROUND

Repair of bones often involves the use of fixation devices to secure the bony anatomy together during the healing process. There are many forms of bone fixation devices including intramedullary devices, pins, screws, plates, and staples. These fixation devices may be formed from a shape memory material, such as nitinol, which creates compression that can augment healing.

SUMMARY

According to one aspect, a surgical spreader assembly and method for use in inserting a bone staple in a patient is disclosed. The surgical spreader assembly includes a first metallic jaw secured to a first polymeric handle and a second metallic jaw secured to a second polymeric handle that is pivotally coupled to the first polymeric handle. The first metallic jaw includes a first hook and a first slot sized to receive a first section of the bone staple. The second metallic jaw includes a second hook and a second slot sized to receive a second section of the bone staple. A spring is positioned between the first polymeric handle and the second polymeric handle, and a locking mechanism is attached to the handles is configured to limit pivoting movement of the handles. The spring biases the first polymeric handle and the second polymeric handle in a closed position. The first polymeric handle and the second polymeric handle are operable pivot about an axis from the closed position to move the first metallic jaw away from the second metallic jaw.

The first metallic jaw and the second metallic jaw may extend in opposite directions to increase the stability of a staple received in the jaw slots. In some embodiments, the spring may be a coil spring, and, in some embodiments, the locking mechanism may include a torsion spring.

Additionally, one or both of the polymeric handles may have a substantially I-shaped or T-shaped cross-section. In some embodiments, the polymeric handles are formed from fiber-reinforced polymeric material. The fibers may be glass or carbon fibers. Each handle may include ribs to facilitate gripping by a user.

The locking mechanism may prevent the handles from being placed in the closed position. In some embodiments, the locking mechanism may include a threaded rod and nut assembly. Additionally, one of the handles may include an open slot to permit the locking mechanism to be quickly disengaged. In some embodiments, the threaded rod and nut are threaded with multiple starts or leads to permit more rapid actuation. In one embodiment, the thread is a triple lead.

In some embodiments, the spreader assembly may also include a stand-off feature such as, for example, a fixed bump or threaded knob) to limit the opening of the spreader. The spreader assembly may include a visual indicator to indicate the extent that the spreader has opened (i.e., the amount that the handles have moved the jaws apart). The first polymeric handle and the second polymeric handles may include a plurality of ribs that define a grip on each handle.

According to another aspect, an instrument for use in inserting a bone staple in a patient is disclosed. The instrument includes a first jaw secured to a first handle and a second jaw secured to a second handle. A spring is positioned between the first polymeric handle and the second polymeric handle.

The first jaw includes a first hook extending a first direction and a first slot sized to receive a first section of the bone staple. The second metallic jaw includes a second hook extending a second direction opposite the first direction and a second slot sized to receive a second section of the bone staple.

The spring biases the first handle and the second handle in a position in which a gap is defined between the first jaw and the second jaw. The first handle and the second handle are operable to pivot about an axis to move the first jaw away from the second jaw to open the gap.

In some embodiments, the gap may extend along a longitudinal axis. The gap may be sized to receive a base of the bone staple when the bone staple is positioned with a longitudinal axis of the base extending parallel to the longitudinal axis of the gap.

In some embodiments, the first jaw and/or the second jaw may be formed from a metallic material. Additionally, in some embodiments, the first handle and/or the second handle may be formed from a polymeric material. In some embodiments, each of the first polymeric handle and the second polymeric handle may be formed from a fiber-reinforced polymeric material. In some embodiments, the spring may be a coil spring positioned between the first polymeric handle and the second polymeric handle.

In some embodiments, the first handle may include a first elongated body that is molded over a shaft of the first jaw, and the second handle may include a second elongated body that is molded over a shaft of the second jaw. In some embodiments, the first elongated body may have a pair of channels defined on opposite sides thereof, and the second elongated body may have a pair of channels defined on opposite sides thereof.

In some embodiments, the instrument may further comprise a locking mechanism attached to the handles that is configured to limit pivoting movement of the handles. In some embodiments, the locking mechanism may include a threaded rod extending between the first handle and the second handle and a retaining nut engaged with the threaded rod and moveable along the threaded rod into engagement and out of engagement with the second handle.

In some embodiments, the second handle may include a slot that is sized to receive the threaded rod, and the threaded rod may be pivotally coupled to the first polymeric handle. The threaded rod may be configured to pivot between a first position in which the threaded rod is received in the slot of the second polymeric handle and a second position in which the threaded rod is spaced apart from the slot of the second polymeric handle.

Additionally, in some embodiments, the instrument may further comprise a torsional spring positioned in the first polymeric handle. The torsional spring may be configured to pre-load the threaded rod in the first position.

In some embodiments, the threaded rod may include a plurality of markings. Each marking may provide a visual indication of the opening of the gap between the first metallic jaw and the second metallic jaw.

According to another aspect, an instrument system is disclosed. The system comprises a bone staple including a base extending along a longitudinal axis and a pair of arms extending outwardly from the base, a first metallic jaw secured to a first polymeric handle and a second metallic jaw secured to a second polymeric handle that is pivotally coupled to the first polymeric handle. The first metallic jaw includes a first hook extending a first direction and a first slot sized to receive a first section of the base of the bone staple. The second metallic jaw includes a second hook extending a second direction opposite the first direction and a second slot sized to receive a second section of the base of the bone staple.

A gap is defined between the first metallic jaw and the second metallic jaw, which extends along a longitudinal axis and is sized to receive the base when the longitudinal axis of the base extends parallel to the longitudinal axis of the gap. The first metallic jaw and the second metallic jaw are positioned between the pair of arms of the bone staple when the first section and the second section of the base are positioned in the first and second slots. The first polymeric handle and the second polymeric handle are operable to pivot about an axis to move the first metallic jaw away from the second metallic jaw to open the gap.

In some embodiments, the system may further comprise a coil spring positioned between the first polymeric handle and the second polymeric handle. In some embodiments, the instrument system may further comprise a locking mechanism attached to the handles that is configured to limit pivoting movement of the handles.

Additionally, in some embodiments, the locking mechanism may include a threaded rod extending between the first polymeric handle and the second polymeric handle, and a retaining nut engaged with the threaded rod that is moveable along the threaded rod into engagement and out of engagement with the second polymeric handle.

In some embodiments, the second polymeric handle may include a slot that is sized to receive the threaded rod. The threaded rod may be pivotally coupled to the first polymeric handle and configured to pivot between a first position in which the threaded rod is received in the slot of the second polymeric handle and a second position in which the threaded rod is spaced apart from the slot of the second polymeric handle.

According to another aspect, a kit for a surgical procedure on a bone of a patient is disclosed. The kit includes a sealed package including a bone staple, a plurality of surgical instruments for preparing a patient's bone for receiving the bone staple, and a surgical spreader assembly for use in inserting the bone staple into the patient's bone. The kit may also include a double polymeric tray configured to contain the sealed package, the plurality of surgical instruments, and the surgical spreader assembly. The double polymeric tray may be contained with an outer box.

BRIEF DESCRIPTION OF THE DRAWINGS

The detailed description particularly refers to the following figures, in which.

DETAILED DESCRIPTION OF THE DRAWINGS

Figure 1:
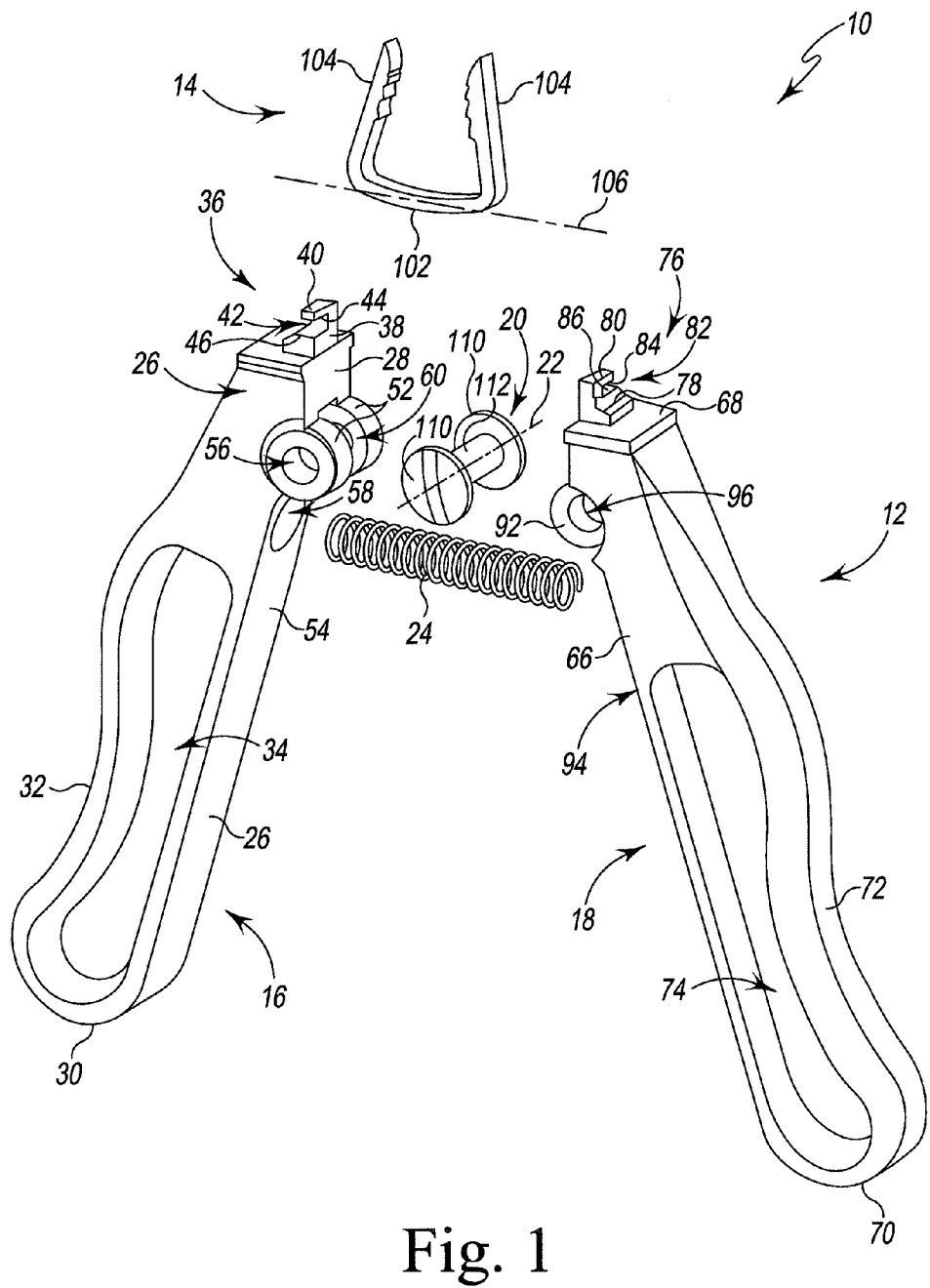
FIG. 1 is an exploded perspective view of one embodiment of a surgical spreader assembly and a fixation device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a surgical instrument system 10 is shown. The surgical instrument system 10 includes a surgical spreader assembly 12 and a fixation device 14. As described in greater detail below, the fixation device is illustratively a staple implant 14, which may be mounted to the spreader assembly 12 for implantation into a patient. Because most surgeries require more than one staple implant, the spreader assembly 12 is included in a kit with a plurality of staple implants.

The spreader assembly 12 includes a pair of handles 16, 18 connected by a post pin 20. The pin 20 has a longitudinal axis 22, and the handles 16, 18 are configured to pivot about the axis 22 between a closed position (see FIG. 3) and an open position (not shown). A biasing element such as a helical spring 24 biases the handles 16, 18 in the closed position.

The handle 16 includes an elongated body 26 extending from a head end 28 to a tip 30. The elongated body 26 is formed from a plastic or polymeric material such as Ultem Hu 1000 plastic resin. A grip 32 sized to be grasped by a surgeon or other user is formed on the elongated body 26, and a channel 34 is defined in each side of the elongated body 26.

The handle 16 also includes a jaw 36 that is secured to the head end 28 of the elongated body 26. The jaw 36 is formed from a metallic material such as, for example, stainless steel.

As shown in FIG. 1, the jaw 36 includes a base 38 and a hook 40 that extends outwardly from the base 38. The hook 40 and the base 38 cooperate to define a slot 42 sized to receive a portion of the staple implant 14. In the illustrative embodiment, the hook 40 has a substantially flat bottom surface 44 that faces a substantially flat top surface 46 of the base 38. The surfaces 44, 46 extend parallel to the top surface of the head end 28.

Figure 3:
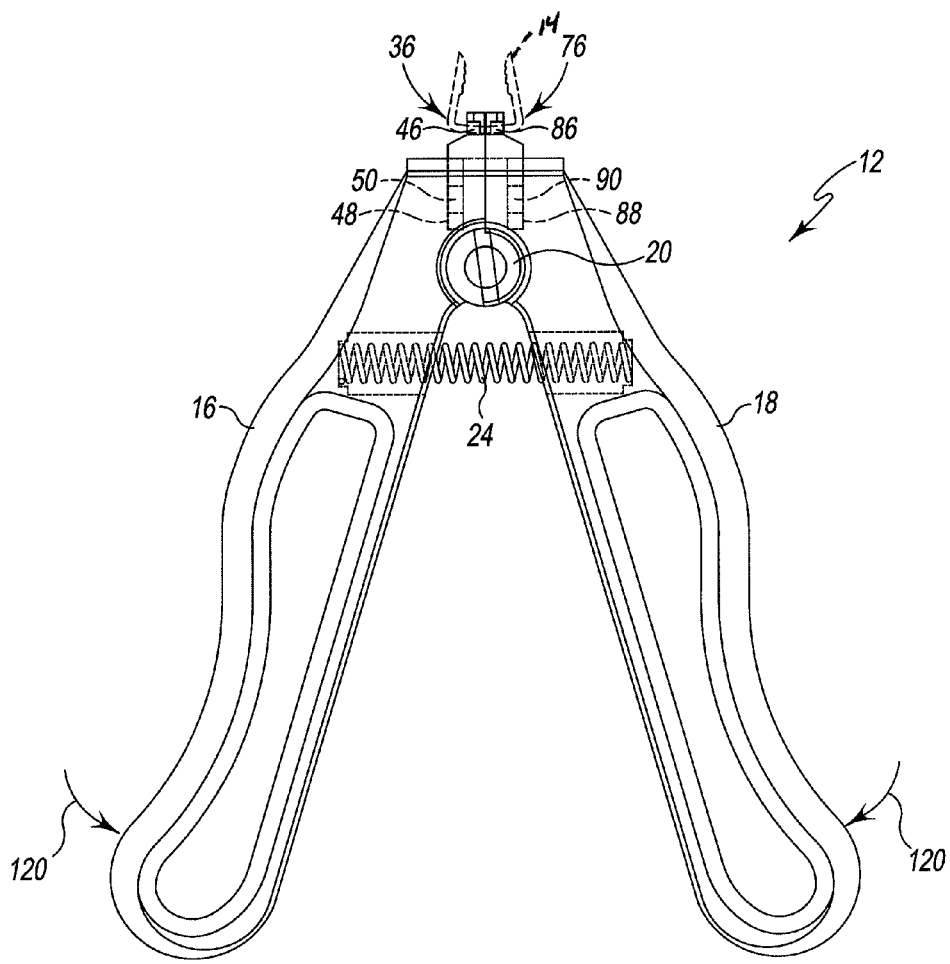
FIG. 3 is a side elevation view of the spreader assembly of FIGS. 1-2.

The jaw 36 includes a shaft 48 that is positioned in the head end 28 of the elongated body 26. As shown in FIG. 3, the shaft 48 extends from the base 38 and includes an elongated slot 50 that is filled with the plastic material forming the elongated body 26. In the illustrative embodiment, the elongated body 26 is formed over the shaft 48 of the jaw 36 via an injection molding process. To do so, the jaw 36 may be placed in a mold. The plastic material in liquid form is injected into the mold and is permitted to flow over the shaft 48 of the jaw 36. The mold is configured such that the base 38 and the hook 40 are isolated from the polymeric material. When the material cools, elongated body 26 is formed over the shaft 48, thereby forming the handle 16.

Returning to FIG. 1, the elongated body 26 also includes a pair of flanges 52 that extend from an inner surface 54 and define a slot 60 therebetween. A pair of through-holes 56, which are sized to receive the post pin 20, are defined in the flanges 52. A closed aperture 58 is defined in the inner surface 54 below the flanges 52. As shown in FIG. 1, the aperture 58 is sized to receive an end of the spring 24.

The handle 18 has a similar configuration to the handle 16. Like the handle 16, the handle 18 includes an elongated body 66 extending from a head end 68 to a tip 70. The elongated body 66 is formed from a plastic or polymeric material such as Ultem Hu 1000 plastic resin. A grip 72 sized to be grasped by a surgeon or other user is formed on the elongated body 66, and a channel 74 is defined in each side of the elongated body 66.

The handle 18 also includes a jaw 76 that is secured to the head end 68 of the elongated body 66. The jaw 76 is formed from a metallic material such as, for example, stainless steel. As shown in FIG. 1, the jaw 76 includes a base 78 and a hook 80 that extends outwardly from the base 78. The hook 80 and the base 78 cooperate to define a slot 82 sized to receive a portion of the staple implant 14. In the illustrative embodiment, the hook 80 also has a substantially flat bottom surface 84 that faces a substantially flat top surface 86 of the base 78. The surfaces 84, 86 extend parallel to the top surface of the head end 68.

The jaw 76 includes a shaft 88 that is positioned in the head end 68 of the elongated body 66. As shown in FIG. 3, the shaft 88 extends from the base 78 and includes an elongated slot 90 that is filled with the plastic material forming the elongated body 66. In the illustrative embodiment, the elongated body 66 is formed over the shaft 88 of the jaw 76 via an injection molding process similar to the one described above in regard to the handle 16.

Returning to FIG. 1, the elongated body 66 of the handle 18 also includes a flange 92 that extends from an inner surface 94. A through-hole 96, which is sized to receive the post pin 20, is defined in the flange 92. A closed aperture (not shown) is defined in the inner surface 94 below the flange 92 and is sized to receive an end of the spring 24.

Figure 2:
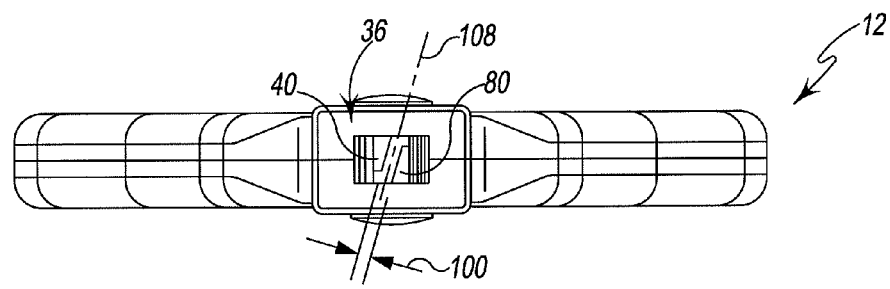
FIG. 2 is a plan view of the spreader assembly of FIG. 1.

As shown in FIG. 1, the hook 80 of the handle 18 faces in the opposite direction from the hook 40 of the handle 16. As shown in FIG. 2, an angled gap 100 is defined between the hooks 40, 80 when the spreader assembly 12 is in the closed position. The gap 100 is sized to permit the passage of the base 102 of the staple implant 14, as described in greater detail below.

As described above, the handles 16, 18 are connected via a post pin 20. The post pin 20 is formed from a metallic material such as, for example, stainless steel. The post pin 20 includes a pair of end plates 110 positioned at the ends of the cylindrical body 112. In the illustrative embodiment, the flange 92 of the handle 18 is positioned in the slot 60 defined between the flanges 52 of the handle 16 such that the through-holes 56, 96 of the handles 16, 18, respectively, are aligned. The cylindrical body 112 of the post pin 20 extends through the holes 56, 96, and the post pin 20 is retained in the holes 56, 96 by the end plates 110, which engage the flanges 52 of the handle 16.

As shown in FIG. 1, the staple implant 14 includes the base 102 and a pair of arms 104 extending outwardly from the base 102. The base 102 has a longitudinal axis 106 that extends traverse to the pair of arms 104. The staple implant 14 is illustrative formed from nickel titanium or nitinol. The arms 104 and the base 102 of the implant 14 have substantially smooth outer surfaces. It should be appreciated that in other embodiments the staple implant 14 may include serrations on the arms 104 to provide additional retention when implanted.

In use, the base 102 of the implant 14 is inserted into the angled gap 100 defined between the jaws 36, 76 of the spreader assembly 12. In particular, the base 102 is positioned such that its longitudinal axis 106 is positioned parallel to the longitudinal axis 108 (see FIG. 2) of the gap 100. The base 102 is then rotated such that the base 102 is received in the slots 42, 82 defined in the jaws 36, 76. A surgeon or other user then applies force in the direction indicated by arrows 120 in FIG. 3 to overcome the bias exerted by spring 24 and pivot the handles 16, 18 about the axis 22. As the handles 16, 18 pivot, the jaws 36, 76 are moved apart, thereby exerting a retention force on arms 104 of the implant 14.

The surgeon may then implant the staple 14 in the desired location. When the staple 14 is properly positioned, the surgeon may release the handles 16, 18. The spring 24 urges the handles 16, 18 to pivot back to the closed position, thereby moving the jaws 36, 76 closer together. The surgeon may then rotate the handle to move the base 102 of the implant 14 out of the slots 42, 82 of the jaws 36, 76 and into the gap 100. The surgeon may then remove the spreader assembly 12.

Figure 4:
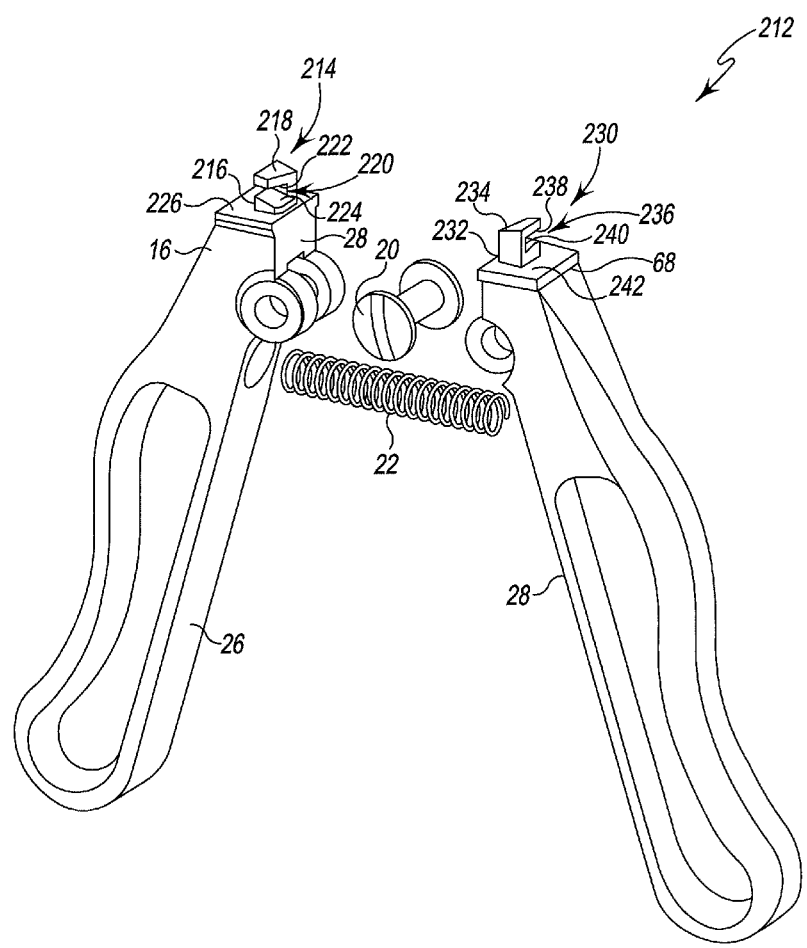
FIG. 4 is an exploded perspective view of another embodiment of a surgical spreader assembly.
Figure 5:
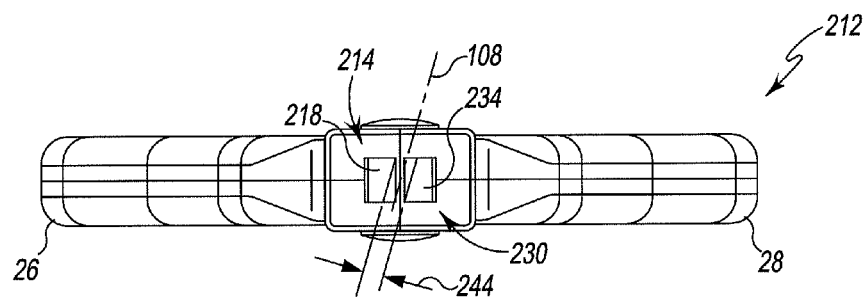
FIG. 5 is a plan view of the spreader assembly of FIG. 4.
Figure 6:
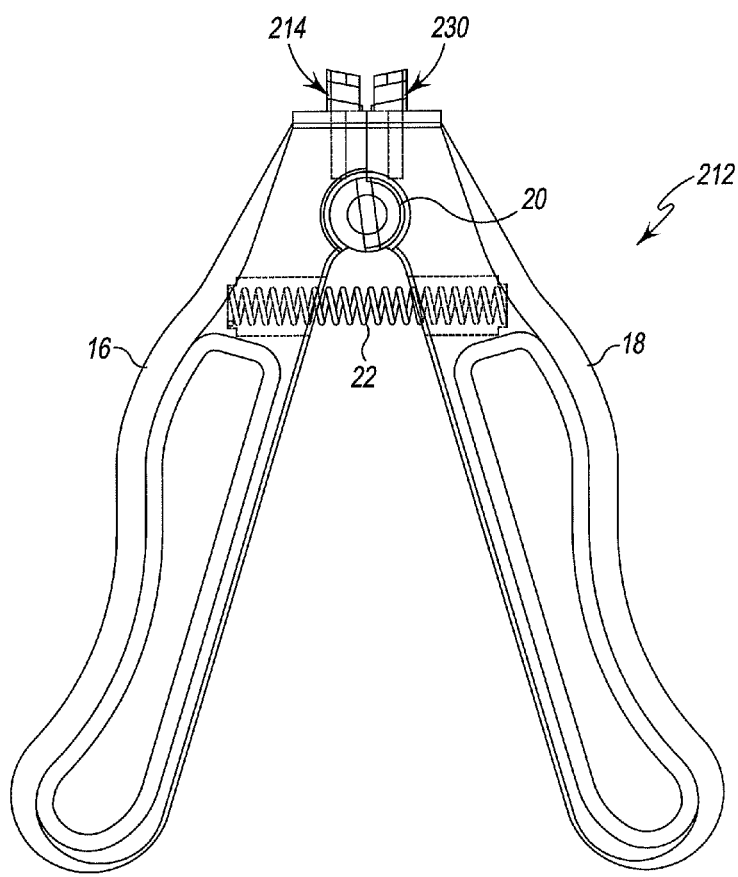
FIG. 6 is a side elevation view of the spreader assembly of FIGS. 4-5.

Referring now to FIGS. 4-6, another embodiment of a spreader assembly (hereinafter assembly 212) is shown. Some of the features of the embodiment of FIGS. 4-6 are similar to the embodiment described above. For such features, the references numbers from the embodiment described above will be used to identify those features in FIGS. 4-6. Like the embodiment of FIGS. 1-3, each of the handles 16, 18 of the assembly 212 is a two-piece handle including a jaw formed from a metallic material and an elongated body formed from a plastic material.

As shown in FIG. 4, the assembly 212 includes a handle 16 that has a jaw 214 secured to an elongated body 26. The jaw 214 is formed from a metallic material such as, for example, stainless steel. As shown in FIG. 4, the jaw 214 includes a base 216 and a hook 218 that extends outwardly from the base 216. The hook 218 and the base 216 cooperate to define a slot 220 sized to receive a portion of a staple implant. In the illustrative embodiment, the hook 218 has a substantially flat bottom surface 222 that faces a substantially flat top surface 224 of the base 216. Those surfaces 222, 224 are angled relative to the top surface 226 of the head end 28 of the elongated body 26.

As shown in FIG. 4, the assembly 212 includes a handle 18 that has a jaw 230 secured to an elongated body 66. The jaw 230 is formed from a metallic material such as, for example, stainless steel. As shown in FIG. 4, the jaw 230 includes a base 232 and a hook 234 that extends outwardly from the base 232. The hook 234 and the base 232 cooperate to define a slot 236 sized to receive a portion of a staple implant. In the illustrative embodiment, the hook 234 has a substantially flat bottom surface 238 that faces a substantially flat top surface 240 of the base 232. Those surfaces 238, 240 are angled relative to the top surface 242 of the head end 68 of the elongated body 66.

As shown in FIGS. 4-6, the hook 218 of the handle 18 faces in the opposite direction from the hook 234 of the handle 16. As shown in FIG. 5, an angled gap 244 is defined between the hooks 218, 234 when the spreader assembly 212 is in the closed position. The gap 244 is sized to permit the passage of the base of a staple implant. The gap 244 is larger than the gap 100 of the embodiment of FIGS. 1-3. As a result, the spreader 212 is capable of being used with larger staples. The spreader 212 may be used in a manner substantially similar to that described above in regard to the spreader 12.

Figure 7:
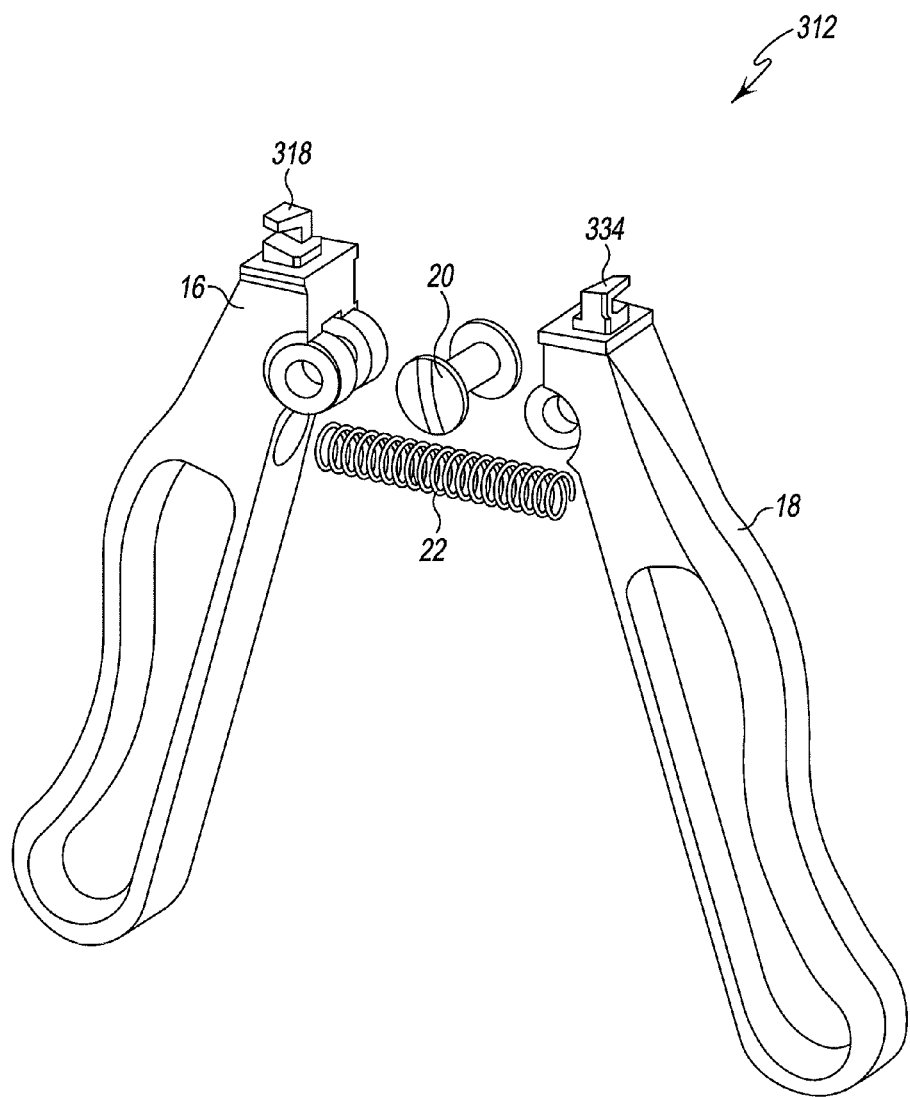
FIG. 7 is an exploded perspective view of another embodiment of a surgical spreader assembly.
Figure 8:
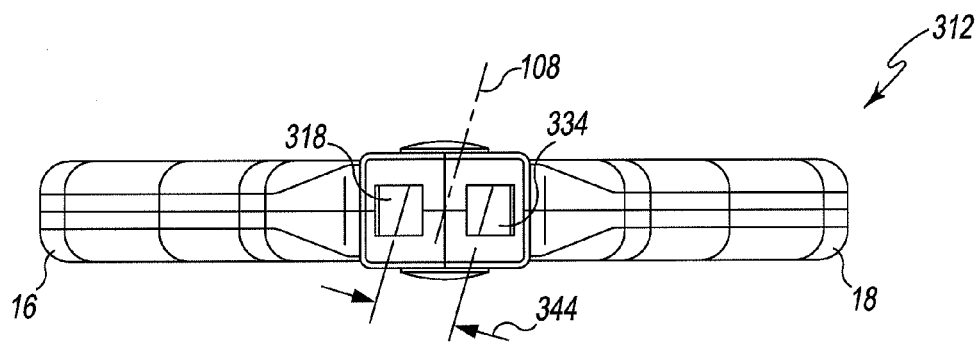
FIG. 8 is a plan view of the spreader assembly of FIG. 7.
Figure 9:
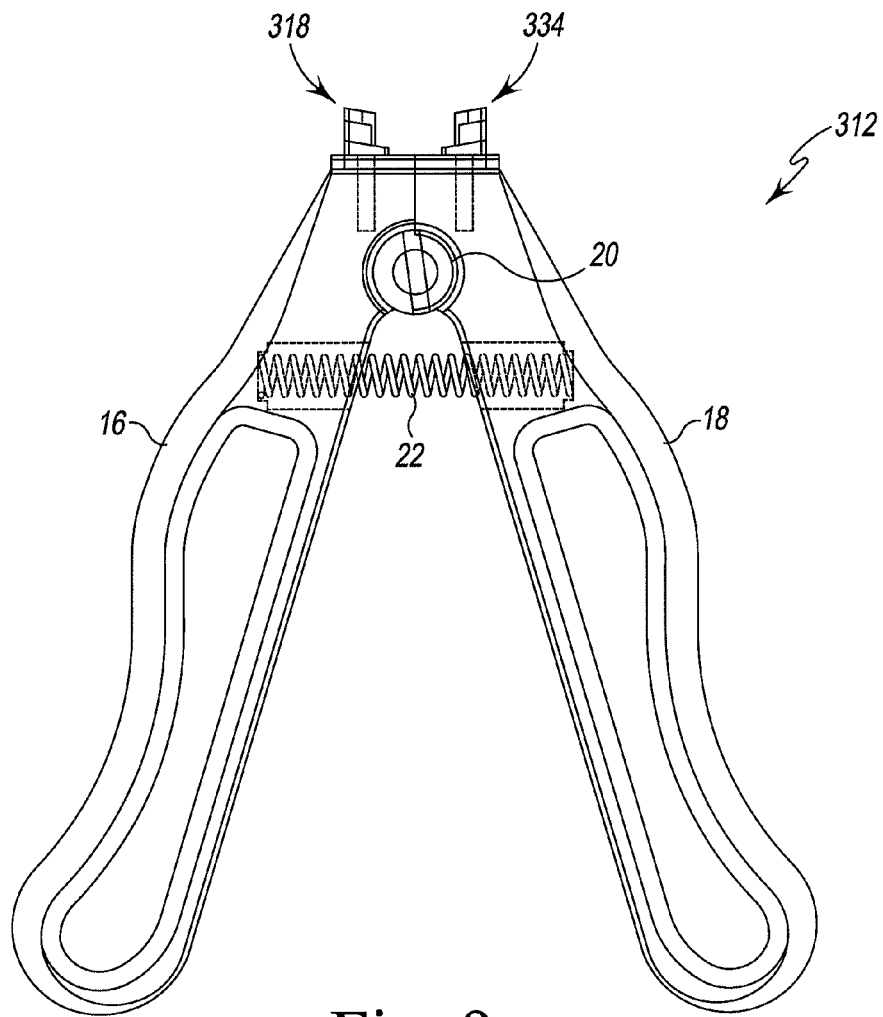
FIG. 9 is a side elevation view of the spreader assembly of FIGS. 7-8.

Referring now to FIGS. 7-9, another embodiment of a spreader assembly (hereinafter assembly 312) is shown. Some of the features of the embodiment of FIGS. 7-9 are similar to the embodiments described above. For such features, the references numbers from the embodiments described above will be used to identify those features in FIGS. 7-9. Like the embodiments of FIGS. 1-6, each of the handles 16, 18 of the assembly 312 is a two-piece handle including a jaw formed from a metallic material and an elongated body formed from a plastic material. As shown in FIG. 8, an angled gap 344 is defined between the hooks 318, 334 of the spreader assembly 312 when in the closed position. The gap 344 is sized to permit the passage of the base of a staple implant. The gap 344 is larger than the gaps 100, 244 of the embodiments of FIGS. 1-6. As a result, the spreader 212 is capable of being used with larger staples.

Figure 10:
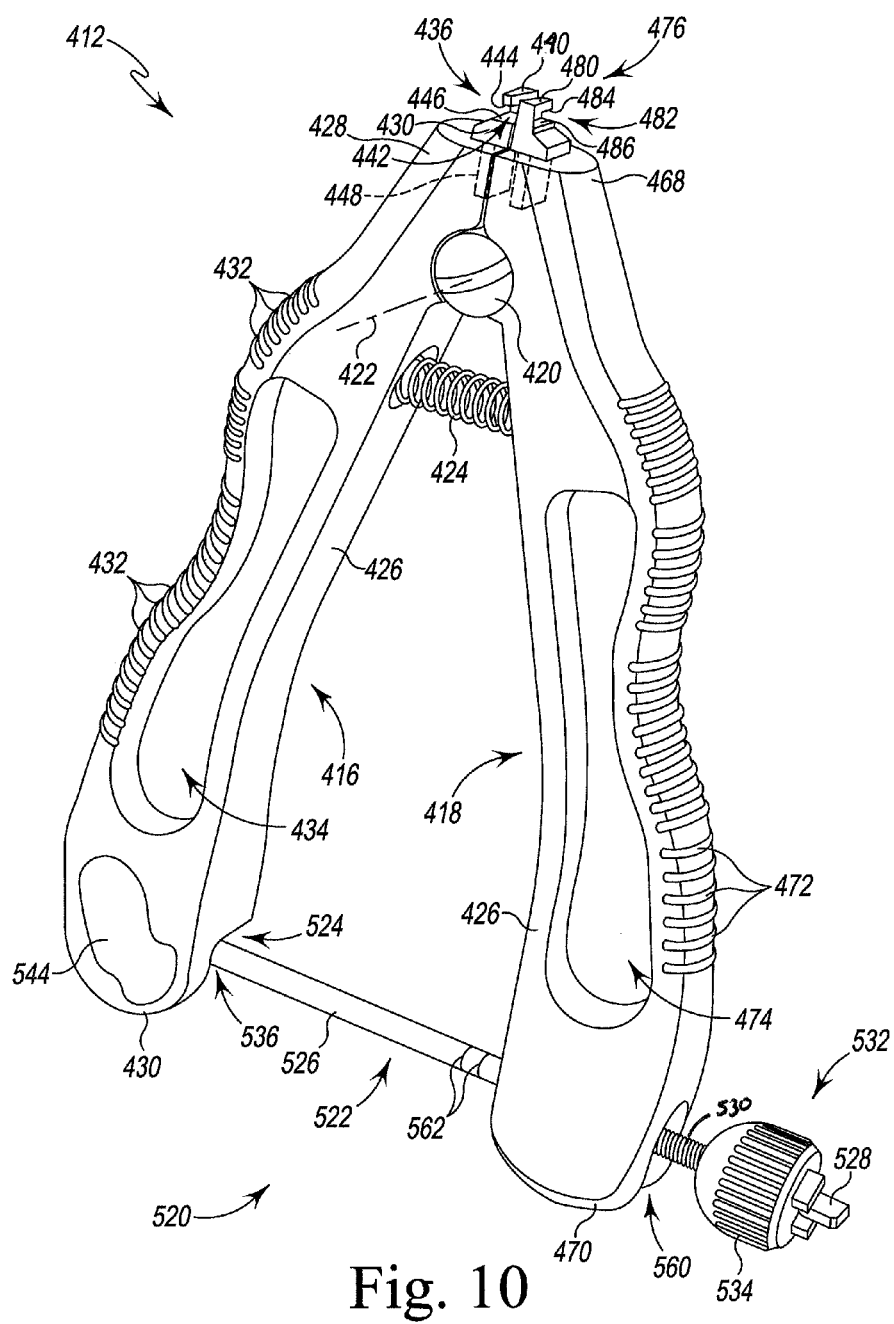
FIG. 10 is a perspective view of another embodiment of a surgical spreader assembly.

Referring now to FIGS. 10-15, another embodiment of a spreader assembly (hereinafter assembly 412) of a system 410 is shown. Some of the features of the embodiment of FIGS. 10-15 are similar to the embodiments described above. For such features, the references numbers from the embodiments described above will be used to identify those features in FIGS. 10-15. As shown in FIG. 10, the assembly 412 includes a pair of handles 416, 418 connected by a post pin 420. The pin 420 has a longitudinal axis 422, and the handles 416, 418 are configured to pivot about the axis 422 between a closed position (see FIG. 10) and an open position (not shown). A biasing element such as a helical or coil spring 424 biases the handles 416, 418 in the closed position.

The handle 416 includes an elongated body 426 extending from a head end 428 to a tip 430. The elongated body 426 is formed from a plastic or polymeric material such as Ultem Hu 1000 plastic resin. A grip including a plurality of ribs 432 sized to be grasped by a surgeon or other user is formed on the elongated body 426, and a channel 434 is defined in each side of the elongated body 426 such that the elongated body 426 has an I-shaped cross-section.

The handle 416 also includes a jaw 436 that is secured to the head end 428 of the elongated body 426. The jaw 436 is formed from a metallic material such as, for example, stainless steel. As shown in FIG. 10, the jaw 436 includes a base 438 and a hook 440 that extends outwardly from the base 438. The hook 440 and the base 438 cooperate to define a slot 442 sized to receive a portion of the staple implant 14 shown in FIG. 1. In the illustrative embodiment, the hook 440 has a substantially flat bottom surface 444 that faces a substantially flat top surface 446 of the base 438. The surfaces 444, 446 extend parallel to the top surface of the head end 428.

The jaw 436 includes a shaft 448 that is positioned in the head end 428 of the elongated body 426. As shown in FIG. 3, the shaft 448 extends from the base 438 and includes an elongated slot 450 that is filled with the plastic material forming the elongated body 426. In the illustrative embodiment, the elongated body 426 is formed over the shaft 448 of the jaw 436 via an injection molding process. To do so, the jaw 36 may be placed in a mold. The plastic material in liquid form is injected into the mold and is permitted to flow over the shaft 448 of the jaw 436. The mold is configured such that the base 438 and the hook 440 are isolated from the polymeric material. When the material cools, elongated body 426 is formed over the shaft 448, thereby forming the handle 416.

Figure 13:
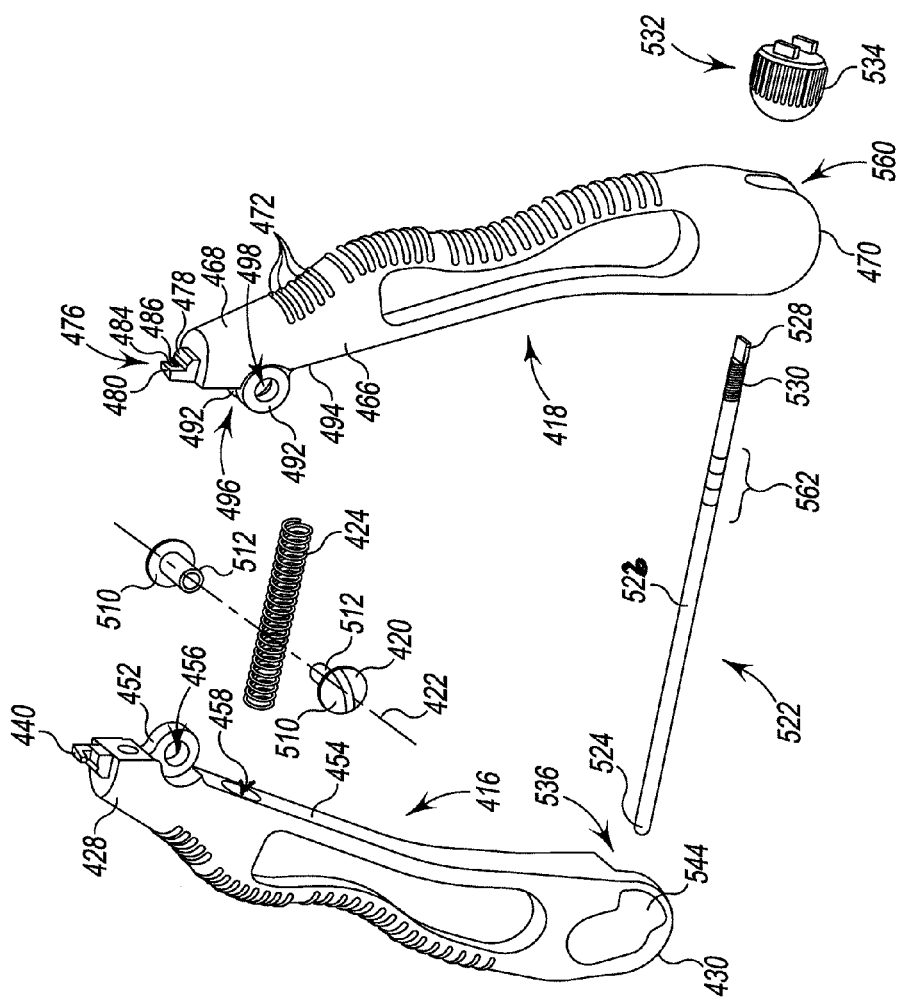
FIG. 13 is an exploded perspective view of the spreader assembly of FIG. 10.

Referring now to FIG. 13, the elongated body 426 also includes a flange 452 that extend from an inner surface 454. A through-hole 456, which is sized to receive the post pin 420, is defined in the flange 452. A closed aperture 458 is defined in the inner surface 454 below the flanges 452. The aperture 458 is sized to receive an end of the spring 424.

The handle 418 has a similar configuration to the handle 416. Like the handle 416, the handle 418 includes an elongated body 466 extending from a head end 468 to a tip 470. The elongated body 466 is formed from a plastic or polymeric material such as Ultem Hu 1000 plastic resin. A grip including a plurality of ribs 472 sized to be grasped by a surgeon or other user is formed on the elongated body 466, and a channel 474 is defined in each side of the elongated body 466 such that the elongated body 466 has an I-shaped cross-section.

The handle 418 also includes a jaw 476 that is secured to the head end 68 of the elongated body 66. The jaw 476 is formed from a metallic material such as, for example, stainless steel. As shown in FIG. 13, the jaw 476 includes a base 478 and a hook 480 that extends outwardly from the base 478. The hook 480 and the base 478 cooperate to define a slot 482 sized to receive a portion of the staple implant 14. In the illustrative embodiment, the hook 480 also has a substantially flat bottom surface 484 that faces a substantially flat top surface 486 of the base 478. The surfaces 484, 486 extend parallel to the top surface of the head end 468.

The jaw 476 includes a shaft 488 that is positioned in the head end 468 of the elongated body 466, as shown in FIG. 3. The shaft 488 extends from the base 478 and includes an elongated slot 490 that is filled with the plastic material forming the elongated body 466. In the illustrative embodiment, the elongated body 466 is formed over the shaft 488 of the jaw 476 via an injection molding process similar to the one described above in regard to the handle 416.

Returning to FIG. 13, the elongated body 466 also includes a pair of flanges 492 that extend from an inner surface 494 and define a slot 496 therebetween. A pair of through-holes 498, which are sized to receive the post pin 420, are defined in the flanges 492. A closed aperture 500 (see FIG. 14) is defined in the inner surface 494 below the flanges 492. The aperture 500 is sized to receive an end of the spring 424.

As described above, the handles 416, 418 are connected via a post pin 420. The post pin 420 is formed from a metallic material such as, for example, stainless steel. The post pin 420 includes a pair of end plates 510 coupled together via a pair of cylindrical bodies 512. In the illustrative embodiment, the flange 452 of the handle 416 is positioned in the slot 496 defined between the flanges 492 of the handle 418 such that the through-holes 456, 498 of the handles 416, 418, respectively, are aligned. The cylindrical bodies 112 of the post pin 20 are secured to one another and extend through the holes 456, 498. The post pin 420 is retained in the holes 456, 498 by the end plates 510, which engage the flanges 492 of the handle 418.

Figure 12:
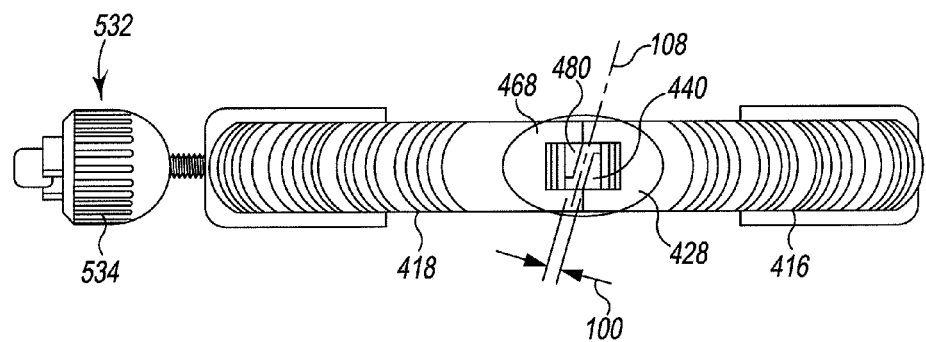
FIG. 12 is a plan view of the spreader assembly of FIG. 10.

As shown in FIG. 12, the hook 480 of the handle 418 faces in the opposite direction from the hook 440 of the handle 416. An angled gap 100 is defined between the hooks 440, 480 when the spreader assembly 412 is in the closed position. The gap 100 is sized to permit the passage of the base 102 of the staple implant 14 and has a longitudinal axis 108.

Returning to FIG. 10, the spreader assembly 412 also includes a locking mechanism 520 that may be used limit the movement of the handles 416, 418. In the illustrative embodiment, the locking mechanism 520 includes a rod 522 that is pivotally coupled to the tip 430 of the handle 416 at its end 524. The rod 522 has a cylindrical shaft 526 that extends from the end 524 to a distal end 528. A plurality of threads 530 are formed on the shaft 526 at the distal end 528, and an internally-threaded locking nut 532 is engaged with the threads 530.

The locking nut 532 includes a grip 534 that a user may grasp to rotate the nut 532 on the shaft 526 to advance the nut 532 axially The locking nut 532 may be advanced along shaft 526 into and out of engagement of with the handle 418. In the illustrative embodiment, the internally-threaded locking nut 532 and the threads 530 include multiple starts or leads to permit rapid movement of the nut 532 along the shaft 526. Illustratively, the internally-threaded locking nut 532 and the threads 530 have a triple lead.

Figure 11:
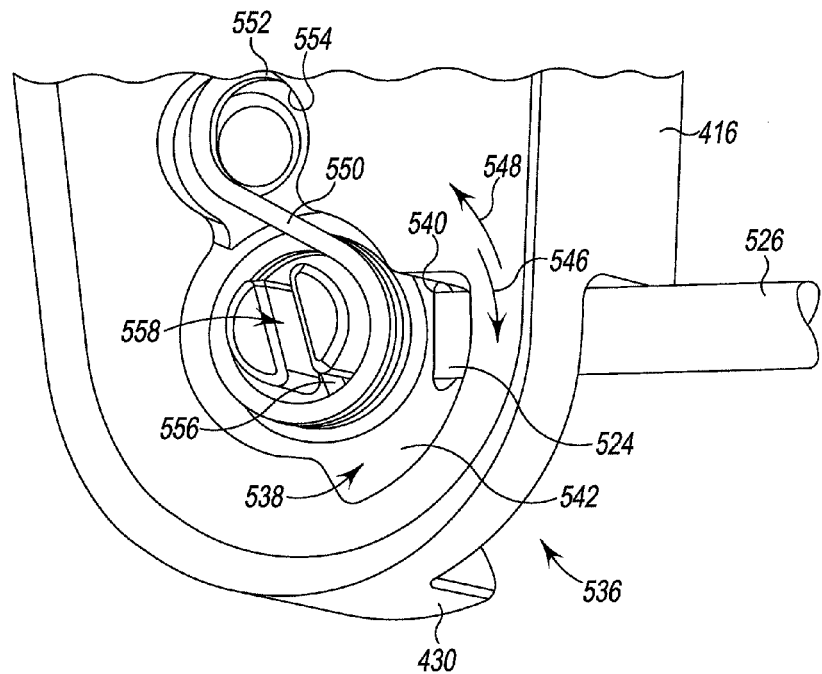
FIG. 11 is a partial cut-away view illustrating a portion of a locking mechanism of the spreader assembly of FIG. 10.

As described above, the rod 522 is pivotally coupled to the handle 416. As shown in FIG. 11, the rod 522 extends through a slot 536 defined in the tip 430 of the handle 416 such that the end 524 of the rod 522 is positioned in an internal pocket 538 defined in the handle 416. In the illustrative embodiment, the end 524 of the rod 522 is received in an aperture 540 of a bobbin 542. The bobbin 542 is retained in the pocket 538 by a cover plate 544 (see FIG. 10) and is permitted to rotate as indicated by arrows 546, 548 in FIG. 11.

A biasing element 550 pre-loads the rod 522 in a position, as described in greater detail below. In the illustrative embodiment, the biasing element 550 is a torsional spring that includes an end 552 engaged with an inner wall 554 of the body 416. Another end 556 is received in a slot 558 defined in the bobbin 542. As shown in FIG. 11, the spring 550 is under tension, which may be released by rotating the bobbin 542 as indicated by arrow 546.

As shown in FIGS. 11 and 13, the tip 470 of the other handle 418 has a slot 560 defined therein. The slot 560 is sized to receive the cylindrical shaft 526 of the rod 522. In the illustrative embodiment, the slot 560 has a downwardly-facing opening.

In use, the base 102 of the implant 14 is inserted into the angled gap 100 defined between the jaws 436, 476 of the spreader assembly 412. In particular, the base 102 is positioned such that its longitudinal axis 106 is positioned parallel to the longitudinal axis 108 of the gap 100. The base 102 is then rotated such that the base 102 is received in the slots 442, 482 defined in the jaws 436, 476. A surgeon or other user then applies force in the direction indicated by arrows 570 in FIG. 14 to overcome the bias exerted by spring 424 and pivot the handles 416, 418 about the axis 22. As the handles 416, 418 are pivoted, the jaws 436, 476 are moved apart, thereby exerting a retention force on arms 104 of the implant 14. The surgeon may monitor the progress of the movement of the jaws 436, 476 using a series of markings 562 arranged axially along the rod 522, which provide a visual indication of the extent of the opening of the jaws 436, 476.

With the jaws 436, 476 opened at a desired position, the surgeon may operate the locking mechanism 520 to prevent the jaws 436, 476 from closing. To do so, the surgeon may rotate the nut 532 to advance the nut 532 along the threads 530 and into engagement with the handle 418. The surgeon may then release the handles 416, 418 as needed, and the nut 532 and rod 522 prevent the handles 416, 418 from closing.

Figure 14:
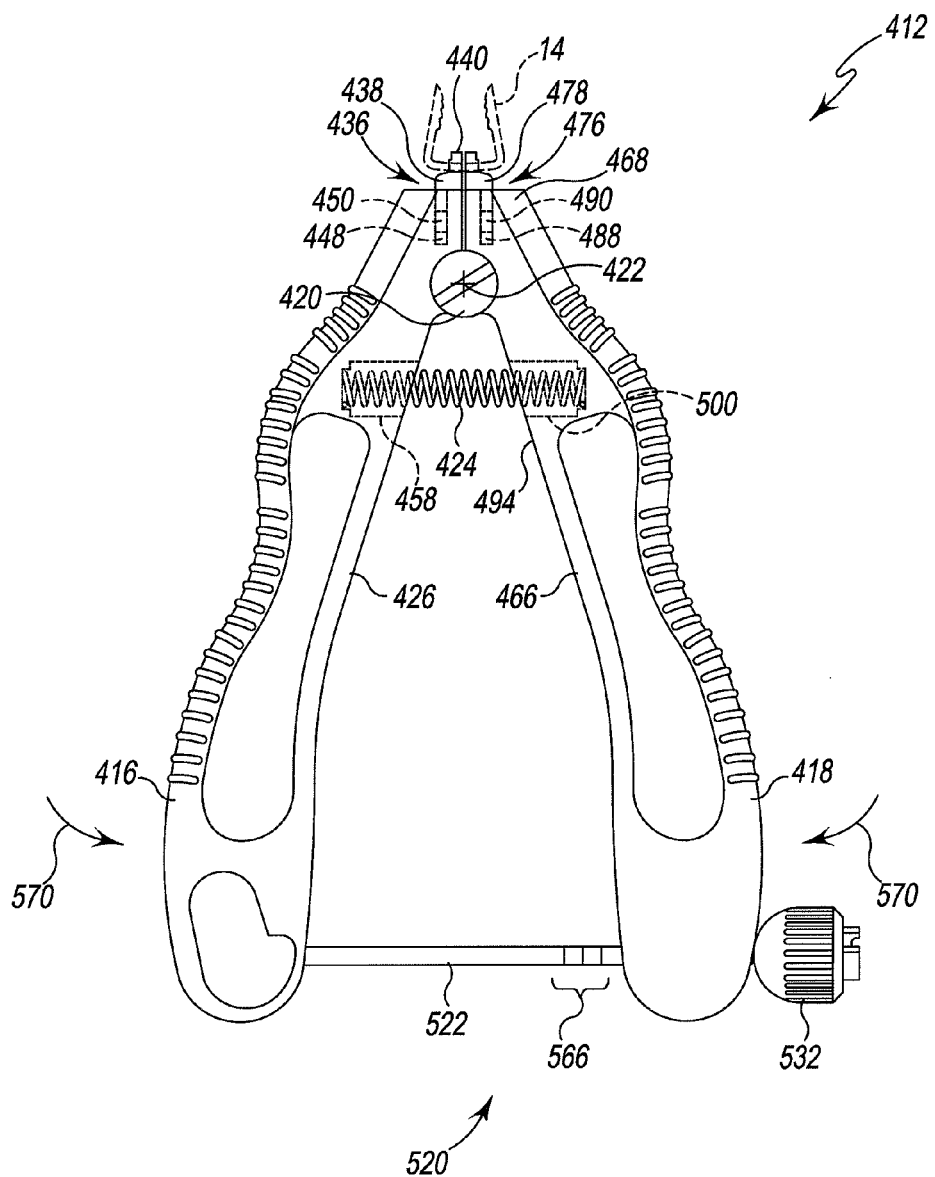
FIGS. 14-15 are elevation views of the spreader assembly of FIG. 10 showing the locking mechanism in two positions.
Figure 15:
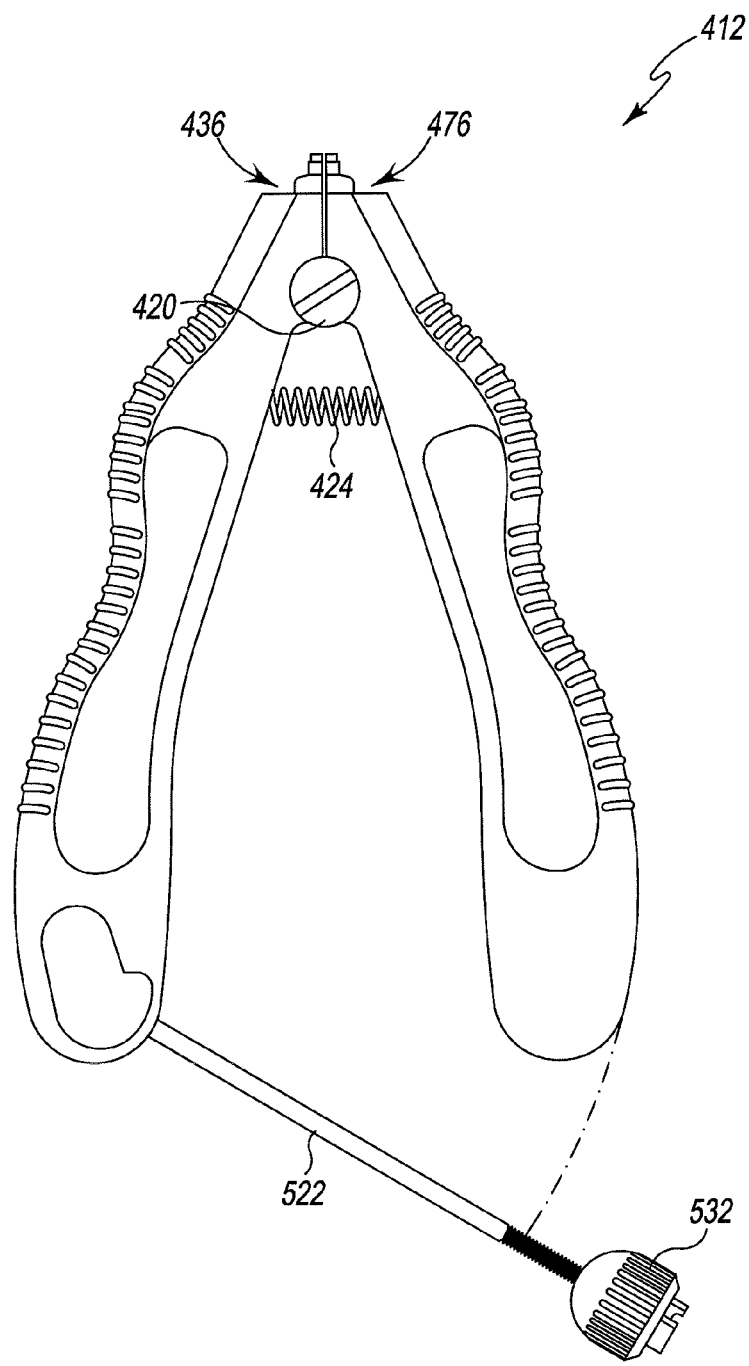

The surgeon may then implant the staple 14 in the desired location. When the staple 14 is properly positioned, the surgeon may release the handles 416, 418. If the locking mechanism 520 is engaged, the surgeon may rotate the nut 532 to move it away from the handle 418 and then pivot the rod 522 as shown in FIG. 15. The torsion spring 550, which is under tension when the rod 522 is positioned as shown in FIG. 14, provides mechanical assistance in urging the rod 522 to pivot. When the locking mechanism is disengaged, the spring 424 urges the handles 416, 418 to pivot back to the closed position, thereby moving the jaws 436, 476 closer together. The surgeon may then rotate the handle to move the base 102 of the implant 14 out of the slots 442, 482 of the jaws 436, 476 and into the gap 100. The surgeon may then remove the spreader assembly 412.

Figure 16:
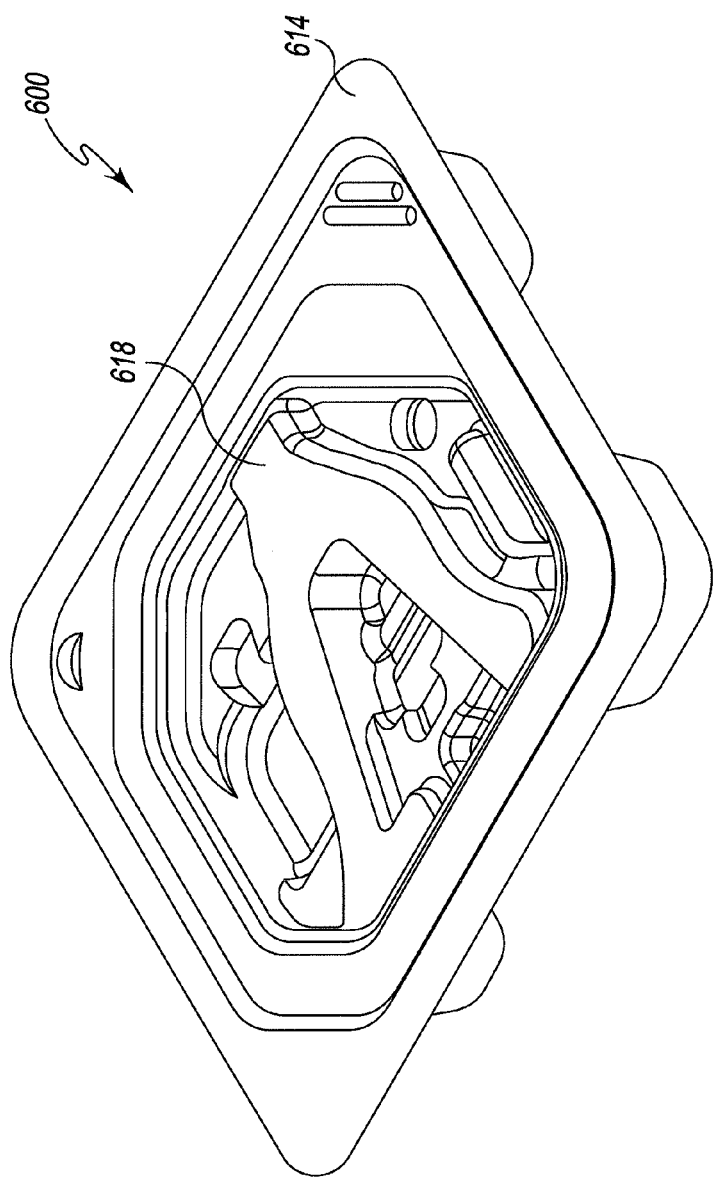
FIG. 16 is a perspective view of a kit including a spreader assembly.
Figure 17:
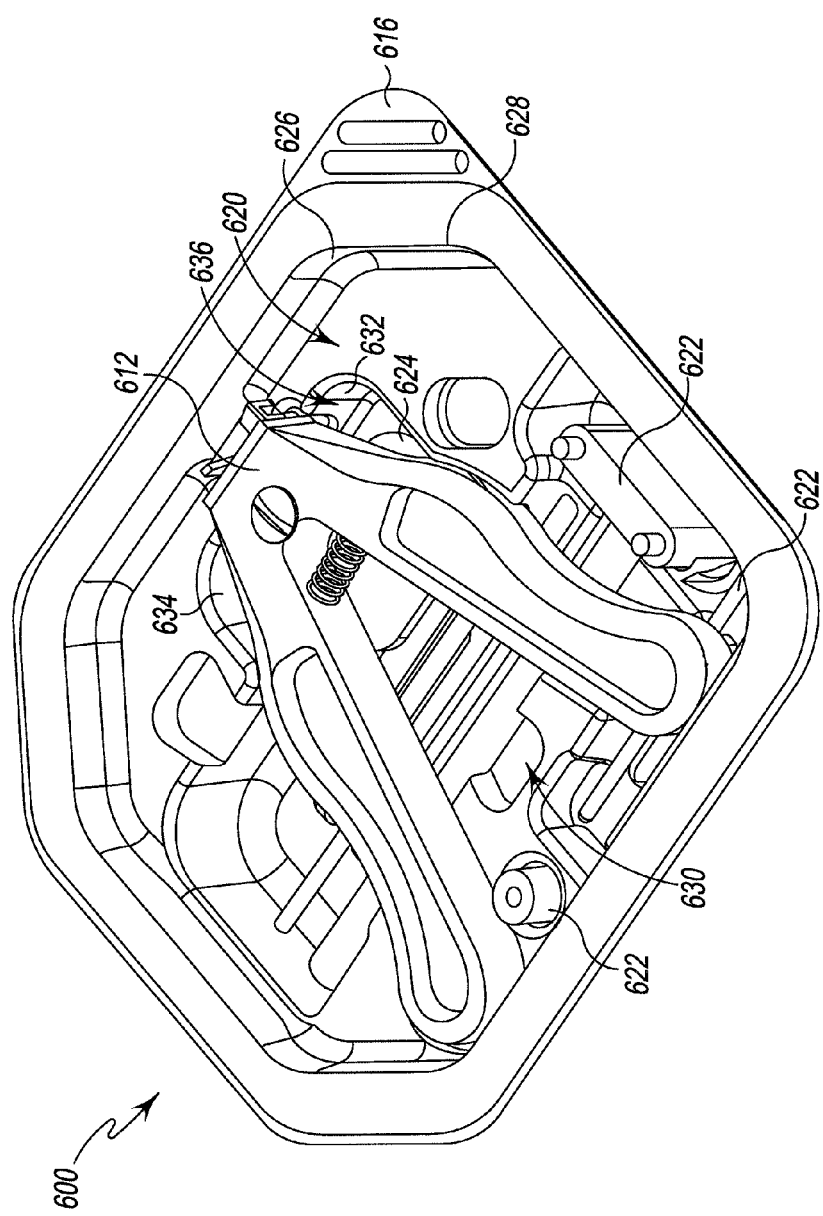
FIG. 17 is another perspective view of the kit of FIG. 16 with a cover removed.
Figure 18:
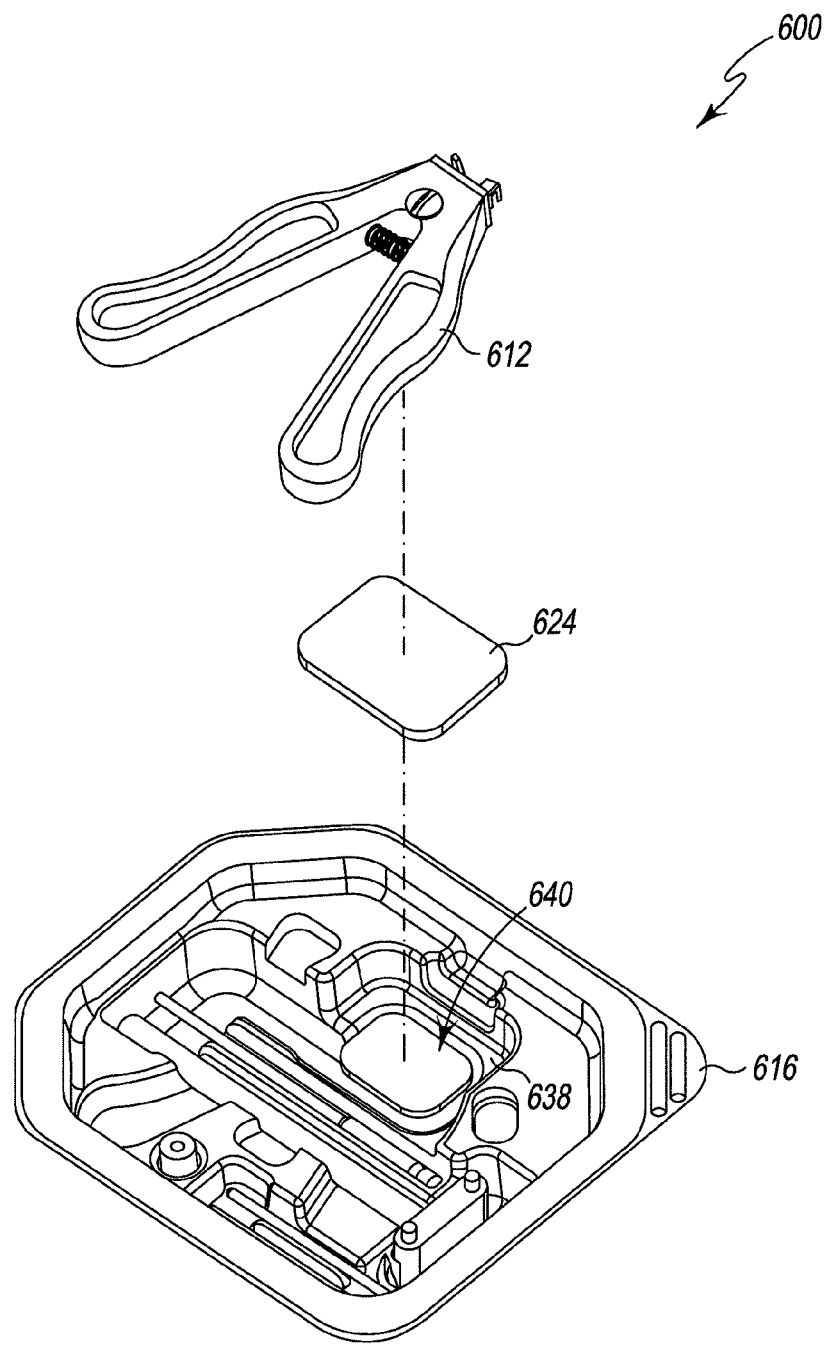
FIG. 18 is an exploded perspective view of the kit of FIGS. 16-17.

Referring now to FIGS. 16-18, a kit 600 for a surgical procedure on a bone of a patient is disclosed. The kit 600 includes a surgical spreader assembly 612 (see FIG. 17), which may take the form of the embodiments described above in regard to FIGS. 1-15. As shown in FIG. 16, the assembly 612 is contained in a pair of polymeric trays 614, 616 and covered by a polymeric cover plate 618. The trays 614, 616 and the plate 618 may be enclosed by an outer box (not shown) for delivery to the operating room or surgical suite. In the illustrative embodiment, the outer tray 614 and the cover plate 618 are formed from an opaque material. The inner tray 616 is formed from a semi-transparent or transparent material such that the assembly 612 is visible through the walls of the tray 616.

Referring now to FIG. 17, the inner tray 616 includes a central cavity 620 that is sized and shaped to receive the spreader assembly 612 and a number of other surgical instruments 622, which are also included in the kit 600 for use in performance of the surgical procedure. The surgical instruments 622 may include a drill, drill guide, positioning pins, and other instruments necessary to prepare the bone. The kit 600 also includes a package or pouch 624 containing one or more staple implants 14, as described in greater detail below.

The cavity 620 is defined by a number of inner walls 626 extending from an opening 628. The inner walls 626 divide the cavity 620 into a number of shaped slots 630 that receive and hold the spreader assembly 612 and other surgical instruments 622. For example, the inner walls 632, 634 define a slot 636 sized to receive the spreader assembly 612 such that the spreader assembly 612 may be positioned in the tray 616 in a single, predetermined location and orientation.

As shown in FIG. 18, the staple package 624 is positioned below the spreader assembly 612 in the tray 616. In the illustrative embodiment, the tray 616 includes a number of inner walls 638 that define a rectangular slot 640 below the slot 636 for the assembly 612. The rectangular slot 640 is sized to receive the staple package 624. In the illustrative embodiment, the staple package 624 is sealed to ensure the cleanliness and sterilization of the staple implants 14.

In use, the kit 600 may be delivered to an operating room or surgical suite prior to the surgical procedure. A user may remove the cover plate 618 and outer polymeric tray 614. The surgeon may use the instruments 622 to surgically prepare a patient's bone to receive a staple 14. The surgeon may then use the surgical spreader assembly 612 to implant the staple 14 as described above in regard to the embodiments of FIGS. 1-15.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An instrument for use in inserting a bone staple in a patient, the bone staple insertion instrument comprising:
   first and second polymeric handles having a proximal end and a distal end opposite the proximal end, a first elongated body extending between the proximal end and the distal end of the first polymeric handle and a second elongated body extending between the proximal end and the distal end of the second polymeric handle;
   a first metallic jaw secured to the first polymeric handle, the first metallic jaw including (i) a first hook extending a first direction, (ii) a first slot sized to receive a first section of the bone staple, and (iii) a distal-facing surface;
   a second metallic jaw secured to the second polymeric handle, the second metallic jaw including (i) a second hook extending a second direction opposite the first direction, (ii) a second slot sized to receive a second section of the bone staple, and (iii) a distal-facing surface; and
   a spring positioned between the first polymeric handle and the second polymeric handle,
   wherein (i) the spring biases the first polymeric handle and the second polymeric handle in a position in which a gap is defined between the first metallic jaw and the second metallic jaw, and (ii) the first polymeric handle and the second polymeric handle are operable to pivot about an axis to move the first metallic jaw away from the second metallic jaw to open the gap, and
   wherein the distal end of the first polymeric handle is molded directly over the distal-facing surface of the first metallic jaw and the distal end of the second polymeric handle is molded directly over the distal-facing surface of the second metallic jaw.

2. The instrument of claim 1, wherein the gap extends along a longitudinal axis, and the gap is sized to receive a base of the bone staple when the bone staple is positioned with a longitudinal axis of the base extending parallel to the longitudinal axis of the gap.

3. The instrument of claim 1, wherein the spring is a coil spring positioned between the first polymeric handle and the second polymeric handle.

4. The instrument of claim 1, wherein the first elongated body has a pair of channels defined on opposite sides thereof and the second elongated body has a pair of channels defined on opposite sides thereof.

5. The instrument of claim 1, wherein each of the first polymeric handle and the second polymeric handle is formed from a fiber-reinforced polymeric material.

6. The instrument of claim 1, further comprising a locking mechanism attached to the handles that is configured to limit pivoting movement of the handles.

7. The instrument of claim 6, wherein the locking mechanism includes:
   a threaded rod extending between the first polymeric handle and the second polymeric handle, and
   a retaining nut engaged with the threaded rod, the retaining nut being moveable along the threaded rod into engagement and out of engagement with the second polymeric handle.

8. The instrument of claim 7, wherein:
   the second polymeric handle includes a slot that is sized to receive the threaded rod; and
   the threaded rod is pivotally coupled to the first polymeric handle, the threaded rod being configured to pivot between a first position in which the threaded rod is received in the slot of the second polymeric handle and a second position in which the threaded rod is spaced apart from the slot of the second polymeric handle.

9. The instrument of claim 8, further comprising a torsional spring positioned in the first polymeric handle, the torsional spring being configured to pre-load the threaded rod at the first position.

10. The instrument of claim 7, wherein the threaded rod includes a plurality of markings, each marking providing a visual indication of the opening of the gap between the first metallic jaw and the second metallic jaw.

11. The instrument of claim 1, wherein each of the first and the second metallic jaws includes a slot and a portion of each of the first and the second polymeric handles extends through the slot of the respective metallic jaw secured thereto.

12. A kit for a surgical procedure on a bone of a patient, comprising:
   a sealed package including a bone staple;
   a plurality of surgical instruments for preparing a patient's bone for receiving the bone staple; and
   the bone staple insertion instrument of claim 1.

13. The kit of claim 12, further comprising a double polymeric tray configured to contain the sealed package, the plurality of surgical instruments, and the bone staple insertion instrument.

14. The kit of claim 12, wherein the bone staple insertion instrument further comprises a locking mechanism attached to the handles and configured to limit pivoting movement of the handles.

15. An instrument system, comprising:
   a bone staple including a base extending along a longitudinal axis and a pair of arms extending outwardly from the base;
   first and second polymeric handles having a proximal end and a distal end opposite the proximal end;

a first metallic jaw secured to a first polymeric handle, the first metallic jaw including (i) a first hook extending a first direction, (ii) a first slot sized to receive a first section of the base of the bone staple, and (iii) a distal-facing surface;

a second metallic jaw secured to a second polymeric handle, the second metallic jaw including (i) a second hook extending a second direction opposite the first direction, (ii) a second slot sized to receive a second section of the base of the bone staple, and (iii) a distal-facing surface, wherein (i) a gap is defined between the first metallic jaw and the second metallic jaw, the gap extending along a longitudinal axis and being sized to receive the base when the longitudinal axis of the base extends parallel to the longitudinal axis of the gap, (ii) the first metallic jaw and the second metallic jaw are positioned between the pair of arms of the bone staple when the first section and the second section of the base are positioned in the first and second slots, and (iii) the first polymeric handle and the second polymeric handle are coupled together and operable to pivot about an axis to move the first metallic jaw away from the second metallic jaw to open the gap, and wherein the distal end of the first polymeric handle is molded directly over the distal-facing surface of the first metallic jaw and the distal end of the second polymeric handle is molded directly over the distal-facing surface of the second metallic jaw.

16. The instrument system of claim 15, further comprising a coil spring positioned between the first polymeric handle and the second polymeric handle.

17. The instrument system of claim 15, further comprising a locking mechanism attached to the handles configured to limit pivoting movement of the handles.

18. The instrument system of claim 17, wherein the locking mechanism includes:
a threaded rod extending between the first polymeric handle and the second polymeric handle, and
a retaining nut engaged with the threaded rod, the retaining nut being moveable along the threaded rod into engagement and out of engagement with the second polymeric handle.

19. The instrument system of claim 18, wherein:
the second polymeric handle includes a slot that is sized to receive the threaded rod, and
the threaded rod pivotally coupled to the first polymeric handle, the threaded rod being configured to pivot between a first position in which the threaded rod is received in the slot of the second polymeric handle and a second position in which the threaded rod is spaced apart from the slot of the second polymeric handle.

20. The instrument system of claim 15, wherein the first polymeric handle and the second polymeric handle include a plurality of ribs that define a grip on each handle.

* * * * *